United States Patent [19]

Deindoerfer et al.

[11] Patent Number: 4,612,614
[45] Date of Patent: * Sep. 16, 1986

[54] METHOD OF ANALYZING PARTICLES IN A FLUID SAMPLE

[75] Inventors: Fred H. Deindoerfer, Northridge; Sherman E. DeForest, Del Mar; Gunner Bolz, Solana Beach, all of Calif.

[73] Assignee: International Remote Imaging Systems, Inc., Chatsworth, Calif.

[ * ] Notice: The portion of the term of this patent subsequent to Jul. 12, 2000 has been disclaimed.

[21] Appl. No.: 512,647

[22] Filed: Jul. 11, 1983

Related U.S. Application Data

[63] Continuation-in-part of Ser. No. 186,418, Sep. 12, 1980, Pat. No. 4,393,466.

[51] Int. Cl.4 .............................................. G06F 15/42
[52] U.S. Cl. ..................................... 364/415; 356/335; 364/497; 364/555
[58] Field of Search ............... 364/415, 497, 499, 510, 364/551, 555; 356/23, 39–40, 244, 335; 358/101, 106, 108

[56] References Cited

U.S. PATENT DOCUMENTS

| | | | |
|---|---|---|---|
| 3,390,229 | 6/1968 | Williams | 356/23 X |
| 3,746,784 | 7/1973 | Van Oosterhout | 358/106 X |
| 3,791,517 | 2/1974 | Friedman | 356/39 X |
| 3,824,393 | 7/1974 | Brain | 356/39 X |
| 3,830,969 | 8/1974 | Hofstein | 356/335 X |
| 4,099,886 | 7/1978 | Oliveira | 356/244 |
| 4,205,384 | 5/1980 | Merz et al. | 364/555 |
| 4,260,258 | 4/1981 | Rose et al. | 356/335 |
| 4,318,180 | 3/1982 | Lundqvist et al. | 364/555 |
| 4,338,024 | 7/1982 | Bolz et al. | 356/23 |
| 4,393,466 | 7/1983 | Deindoerfer et al. | 364/415 |

OTHER PUBLICATIONS

V. Kachel, et al. "Fast Imaging In Flow: A Means of Combining Flow-Cytometry and Image Analysis" *The Journal of Histochemistry & Cytochemistry*, vol. 27, No. 1, pp. 335–341, 1979.

David B. Kay, et al. "Imaging In Flow" *The Journal of Histochemistry & Cytochemistry*, vol. 27, No. 1, pp. 329–334, 1979.

Myron R. Melamed, et al. "An Historical Review of the Development of Flow Cytometers and Sorters".

*Primary Examiner*—Gary V. Harkcom
*Attorney, Agent, or Firm*—Limbach, Limbach & Sutton

[57] ABSTRACT

A method for analyzing particles and particularly sediments of urine is accomplished by distributing the sample over an extended area. A plurality of optical still images is taken of the sample, with each image representing a different portion of the area. Each optical image is converted into an electronic image, with the images of the particles in the electronic images. The images of the particles are extracted from the electronic images. The images of the particles are displayed in an ordered array by classes of visually discernible characteristics.

26 Claims, 4 Drawing Figures

METHOD OF ANALYZING PARTICLES IN A FLUID SAMPLE

TECHNICAL FIELD

This application is a continuation-in-part application of a U.S. patent application Ser. No. 186,418 filed on Sept. 12, 1980, now U.S. Pat. No. 4,393,466.

The present invention relates to a method of analyzing particles in a fluid sample and more particularly to a method of analyzing biological fluid samples, such as urine, that are dilute, but without the necessity of physically creating a concentrated sample for analysis.

BACKGROUND ART

Heretofore the method for urine sediment examination requires the following steps: (i) urine must be poured into a tube and spun down in a centrifuge to separate the sediment from its suspending fluid; (ii) most of the cleared suspending fluid must be poured out; (iii) the sediment must be resuspended in the remaining fluid; (iv) the suspension must be transferred to and spread on a microscope slide; (v) a cover slip must be placed over the suspension on the slide; (vi) the slide must be focused under a microscope; and (vii) a number of fields of view must be searched and examined for the presence of abnormal numbers of red and white blood cells, epithelial cells, casts, bacteria, yeast, parasites, mucoid threads, crystals, etc., which compose urine sediment in various proportions depending upon the presence of disease. The steps of centrifugation (i), decantation (ii) and resuspension (iii) are used because the fluid sample is dilute. All these steps are currently performed manually. The manipulations involved frequently make the method messy and unpleasant. Spreading of the sediment suspension on the microscope slide often is uneven with particles overlapping one another. When numerous sediments are viewed, prolonged peering into the eyepieces of a microscope becomes tiring. All these factors contribute to imprecision.

Other apparatus for handling biological specimens include the so-called Coulter counter. In this counter blood cells are passed in single file through an orifice and detected and counted by the manner in which they change the electric properties at the orifice. However, information from the Coulter counter is limited to the analysis of a single type of measurement. Where multiple parameter information is desired, the standard commercial way of obtaining it is by preparing a microscope slide with the cells fixed on an image plane and having a human operator or pattern recognition machine count statistically significant numbers of the cells as the cells are observed one-at-a-time on the slide through a microscope.

Other attempts have been made in recent years to provide optical analysis of particles flowing in a flow stream. For instance, Kay, et al., *Journal of Histochemistry and Cytochemistry*, Volume 27, page 329 (1979) shows a Coulter type orifice for moving cells in single file with the cells magnified on a vidicon. Additionally, Kachel, et al., *Journal of Histochemistry and Cytochemistry*, Volume 27, page 335, shows a device for moving cells in single file through a microscopic area where they are photographed. See also for instance *Flow Cytometry and Sorting*, Melamed et al., John Wiley & Sons 1979, Chapter 1.

U.S. Pat. No. 4,338,024 issued on July 6, 1982 discloses an apparatus and a method for quantitative analysis of particle information.

However, none of the references cited heretofore teach or suggest a solution to the problem of analysis of particles in a dilute fluid sample, without the necessity of initially creating a concentrated sample through centrifugation, decantation and resuspension.

DISCLOSURE OF THE INVENTION

A method of analyzing particles from a fluid sample containing the particles, comprises distributing the sample over an extended area. A plurality of optical still images of the sample over the area are taken, with each optical image representing a different portion of the area. Each of the optical images is converted into an electronic image with the images of the particles in the electronic images. The images of the particles are extracted from the electronic images and are displayed in an ordered array by classes of visually discernible characteristics.

DETAILED DESCRIPTION OF THE INVENTION

The method of the present invention comprises distributing over an extended area a fluid sample containing particles, such as urine. The distribution can be done, for example, by smearing the sample over a microscope slide, such that the particles substantially do not overlap one another. A plurality of optical still images of the sample are taken, with each image representing a different portion of the slide. Thus, for example, the slide with the sample thereon may be mounted in a microscope such that a portion of the slide is in the imaging area as the slide is moved about. Each image will be of a different portion of the slide. Each of the optical images is converted to an electronic image. The images of the particles are in the electronic images. The images of the particles are extracted and composited from the electronic images. The images of the particles are then displayed in an ordered array by classes of visually discernible characteristics.

Figure 1:
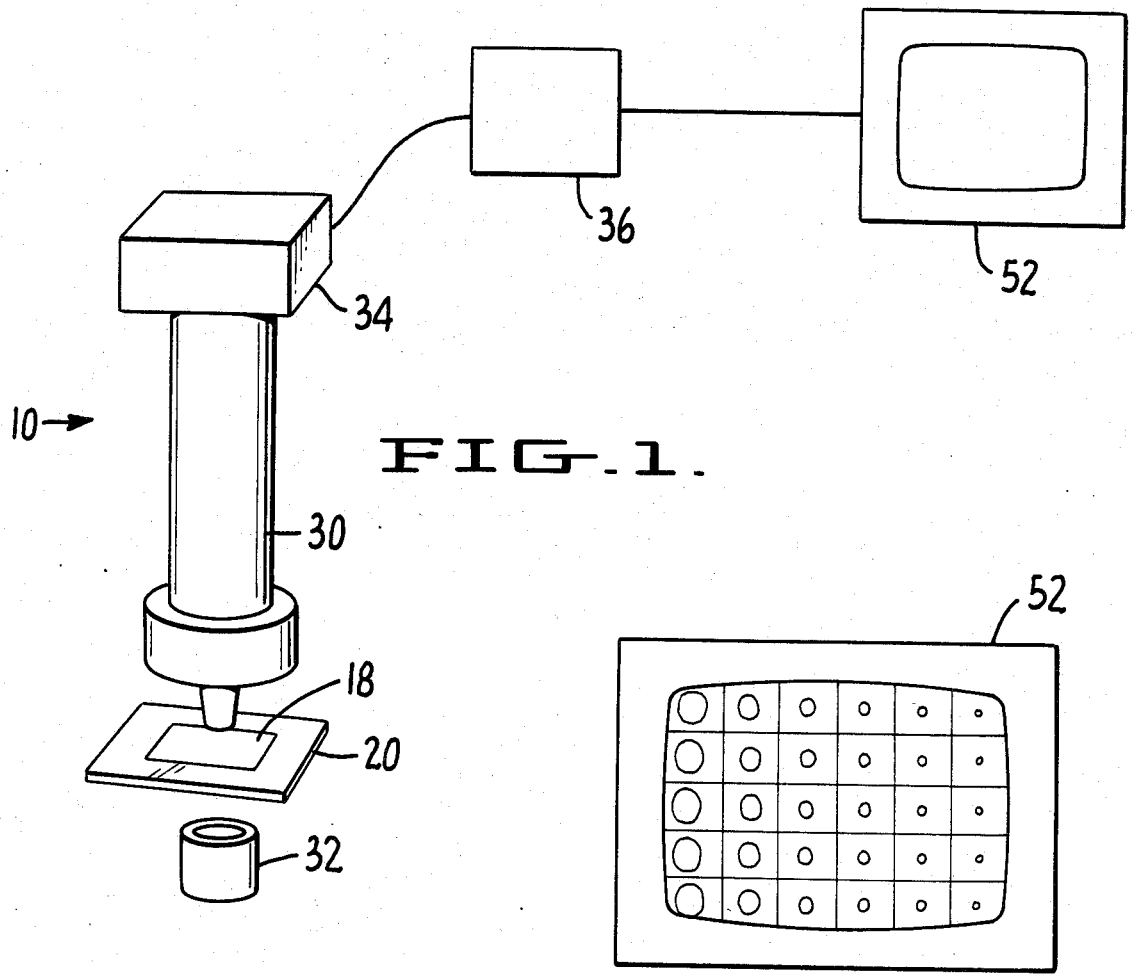
FIG. 1 is a perspective view of an apparatus which can be used with the method of this invention.

The method of the present invention can be practiced by using an apparatus 10, shown in FIG. 1. The apparatus 10 includes a microscope 30 which is focused on an examination area 18 of the microscope slide 20. The examination area 18 is illuminated from below by a strobe light 32 which is preferably a U.S. Scientific Instrument Corporation Model 3018 containing a 2UP1.5 lamp. The light 32 is directed at the microscope 30 in a direction substantially parallel to the thickness of the slide 20. The strobe light 32 operates, preferably, at one-sixtieth of a second, thereby forming a series of still optical images at the microscope 30. The output of the microscope 30 is focused on a vidicon camera 34 which is preferably a camera model number KY 1900 manufactured by JVC. The camera 34 converts each optical image into an electronic image. The analog-to-digital converter associated with the camera 34 also segments each of the electronic images into a plurality of pixels, with each pixel corresponding to a defined portion of each image. The plurality of electronic images (each optical image is converted into an electronic image) contain images of the particles. Since the biological fluid is dilute, it is possible that not every electronic image contains an image of a particle or particles.

The electronic images are then passed from the camera 34 to the processor 36. The processor 36 extracts from each electronic image the images of the particles. The images of the particles are displayed on display 52 in an ordered array by classes of visually discernible characteristics.

Figure 1A:
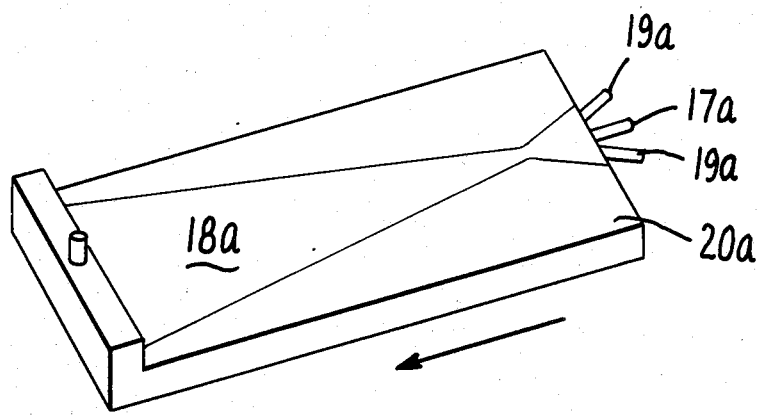
FIG. 1A is a perspective view of a flow chamber suitable for use with the apparatus of FIG. 1 for the method of this invention.

The method of the present invention can also be practiced by the use of a flow cell 20a, shown in FIG. 1A. The flow cell 20a is of the type fully described in U.S. Pat. No. 4,338,024. A sample fluid, such as urine, is sent into the flow cell 20a through first input 17a. Sheath fluids are provided to the flow cell 20a through the second inputs 19a. The sample fluid is moved through the flow cell 20a in the direction shown by arrow A. The sample fluid is distributed over an extended area 18a, which has a width many times the thickness, with each measured perpendicular to the direction of flow. The sample fluid is distributed such that the particles substantially do not overlap one another in the extended area 18a. The sample fluid in the flow cell 20a is placed under the microscope 30 with the microscope 30 focused on the extended area 18a. As the sample fluid moves through the flow cell 20a, the microscope 30 takes an optical image of the fluid in the viewing area 18a. Since the fluid is moving, the apparatus 10 is held stationery. Thus, the images formed at the microscpe 30 are of different portions of the sample fluid.

Figure 2:
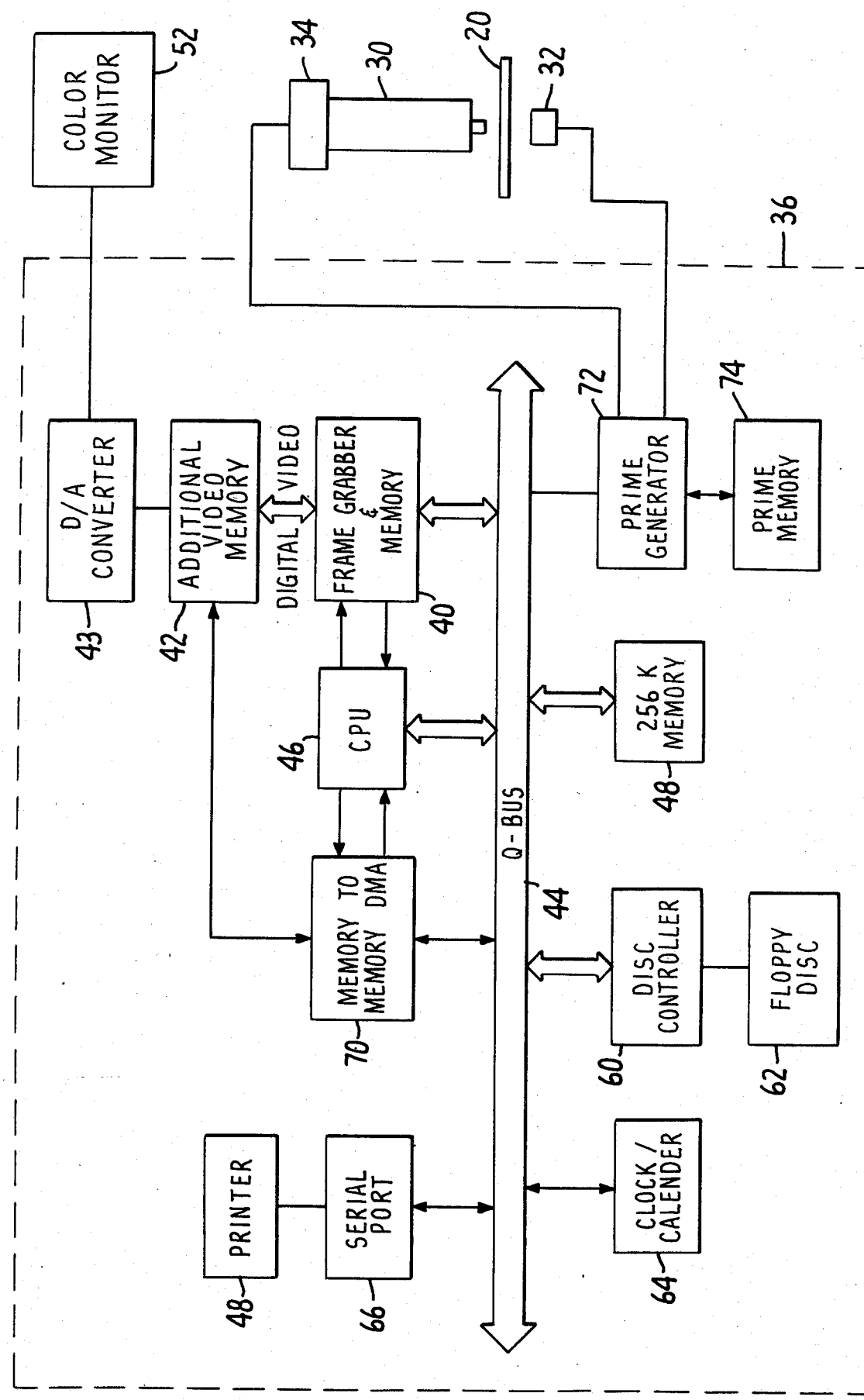
FIG. 2 is a schematic block diagram of a processor employed by the apparatus of FIG. 1.

The processor 36 is shown in greater detail in block schematic form in FIG. 2.

The processor 36 includes a frame grabber and memory 40 which receives the electronic image from the camera 34. The frame grabber 40 can be a module which is available from Matrox Corporation of Montreal. Preferably, the frame grabber 40 is a Model 101-0009 CRT/IO Module from International Remote Imaging Systems, Inc. of Chatsworth, Calif. The output of the frame grabber and memory 40 is supplied to an Additional Refresh Video Memory 42, which comprises a 64K dual ported luminance memory and a 32K dual ported R-Y and B-Y memory. The output of the Refresh Video Memory 42 is connected to a D/A converter 43 which is coupled to the color monitor 52.

The Frame Grabber and Memory 40 is also coupled to a Q-Bus 44 of the Central Processing Unit 46, which is preferably a Telesoft T68 Central Processing Unit. 256K of memory 48 from Chrislin Industries Inc. is also connected to the Q-Bus 44. In addition, a disc controller 60, with a floppy disc drive 62 attached thereto, is also connected to the Q-Bus 44. The processor 36 also comprises a clock/calendar 64 connected to the Q-Bus 44. A serial port 66 with a printer 68 are also connected to the Q-Bus 44. A Memory-to-Memory DMA 70 connects the Additional Video Memory 42 to the Q-Bus 44. Finally, a prime generator 72 with a prime memory 74 are also connected to the Q-Bus 44. The prime generator 72 also activates the strobe 32.

Each electronic image from the camera 34 is stored in the Frame Grabber and Memory 40. The CPU 46 operates on the electronic image received by the processor 36. The processed images are stored in the Memory 42 which are supplied to the Monitor 52 for display. For long term storage, the images can be stored on the floppy disc 62. The prime generator 72 detects the edge of the particle in the electronic image. The operation of the prime generator 72 is the subject of U.S. application, Ser. No. 470,208, filed Feb. 28, 1983, now U.S. Pat. No. 4,538,299 and is incorporated herein by reference.

One variation of the method of the present invention is by forming a resultant image from the electronic images, which comprises a plurality of the images of the particles. The images of the particles are arranged in an ordered array. The resultant image is then displayed.

A wide variety of programming may be employed for further processing each electronic image or the one resultant electronic image with the apparatus of FIG. 2 depending upon the particular task which user wishes to perform.

For example with urine, in the method of the prior art, if chemical particles, such as amorphous phosphates are in the imaging area and obscure the view of the biological particles, the phosphate particles are removed chemically through the addition of hydrochloric acid. With the method of the present invention, however, the chemical particles may be removed electronically, i.e. through image processing techniques. If it is desired to remove particles of particular size, color or shape from view, this may be done electronically without repreparing the sample each time. Moreover, with the method of the present invention, biological particles which heretofore may not be removed chemically, may be similarly electronically removed from the image. Thus a greater degree of flexibility is possible with the present invention.

In addition, the background image can be subtracted from each electronic image before the images of the particles are composited. Alternatively, the resultant image is formed and then the background image is subtracted from each image of the particles that forms the resultant image.

Figure 3:
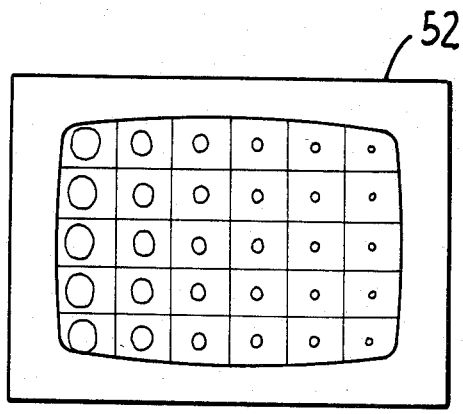
FIG. 3 is a sample of a display showing images of particles arranged in an ordered array by classes of visually discernible characteristics.

The images of the particles are displayed on display 52 in an ordered array. By an ordered array, it is meant that images of particles are displayed by classes, each class having a visual characteristic different from the other class. For example, the images can be displayed by size, i.e., the images of the same size particles (presumably representing the same type of particle) are displayed in the same row or same column. An adjacent row or column on display 52, being a different class, will be displayed images of particles having a different size. The visual presentation of images of particles in an ordered array facilitates identification of the type of particle by the user. Apart from size, the display of the images of the particles can be by color, shape or texture (i.e. internal detail of the particle), or any other visually distinguishable characteristic. An example of such a display is shown on FIG. 3.

The resultant image can also comprise a plurality of images of particles, that are only a certain class or classes of images of particles. For example, a resultant image can be formed with a plurality of images of particles which are characterized by being limited within a range of the size of the particles. Alternatively, the resultant image can be formed with a plurality of images of particles, with an a priori determined class of particles, the images of which are not composited to form the resultant image. In other words, for example, a resultant image can be composited from a plurality of images of particles in an ordered array, such that an a priori determined class of particles, such as a particular size of particles, are not used to form the resultant image.

The images of the particles can be matted for further ease of viewing and identification.

In another embodiment of the method of the present invention, the display 52 can be a unit manufactured by Elo-Graphics, Inc. Such a display unit 52 has a touch screen, i.e., the display screen can accept tactile feedback signal(s) from the user. When the images of the particles are displayed in an ordered array, the user can edit, i.e., remove from the display those images of the particles that do not belong in the particular class. This is accomplished by touching the touch screen in the particular area where the image of the particle is to be edited. The processor 36 acknowledges the activation of the screen 52 by the user and deletes from that portion of the display where the user has touched the screen. In this manner, misclassified particles can be rectified.

Furthermore, because the display 52 is connected to the processor 36, which retains a count of the number of particles in each class, any editing of the images on the screen of display 52 can also edit the number of particles in each class, stored in processor 36. For example, a sample of urine is examined under the microscope 30. A plurality of optical images are formed with each optical image converted into an electronic image. The portion of each electronic image containing the image of a particle is extracted and is stored on disc 62. The processor 36 determines there are 320 particles of Size A, among others. Because the display 52 has a limited area, the processor 36 displays only sixteen (16) images of particles of Size A. It is assumed that the sixteen images are statistically representative of the 320 images of the particles of Size A. Upon presentation of the sixteen images on display 52, the user can edit the images of the particles of Size A. If, for example, two (2) images of particles of Size A are removed, as discussed above, the processor 36 applies this factor and multiplies the total count accordingly. Therefore, the new count of the number of particles of Size A would be (14/16×320=280). Thus, with the method of the present invention, manual editing of the images of particles that are presented for viewing is achieved with machine editing of the total count of the number of particles based upon the manual edit.

It should be appreciated that there are many advantages to the method of the present invention. The first and foremost is that the analysis of particles of a dilute sample may be made without first physically creating a concentrated sample, with its attending problems of centrifugation, decantation and resuspension. The method of resuspension of the prior art results in overlap of the various particles or results in a biased image. With the method of the present invention, the fluid is more statistically representative of the particles with less likelihood of overlap of the particles, and there is no bias of the image. Next, it should be appreciated that the degree of apparent concentration may be varied electronically. In addition, the elimination of manual handling steps saves time, potential sources of error and offers biological safeguards (potentially infectious samples are analyzed with a minimum of human handling).

Then too, consumable items, such as tubes, pipettes and microscope slides, are not used resulting in economic savings. Finally, with the image in electronic form, a number of imaging techniques may be used to further process the image, including the electronic removal or accumulation of specific chemical and biological particles.

What is claimed is:

1. A method of analyzing particles from a fluid sample containing said particles comprising:
   distributing said fluid sample over an extended area with substantially no particle overlapping other particles;
   forming a plurality of optical still images of said sample, including said particles, over said area, with each optical still image representing a different portion of said area;
   converting each of said optical still images to an electronic image thereby converting optical still images of said particles into electronic images of said particles;
   extracting images of said particles from said electronic images; and
   displaying said electronic images of said particles in an ordered array by classes of visually discernible characteristics.

2. The method of claim 1, wherein one of said visually discernible characteristics is size of said particles.

3. The method of claim 1, wherein one of said visually discernible characteristics is color of said particles.

4. The method of claim 1, wherein one of said visually discernible characteristics is shape of said particles.

5. The method of claim 1, wherein one of said visually discernible characteristics is texture of said particles.

6. The method of claim 1 further comprising the step of
   editing said display of said images of said particles.

7. The method of claim 6 further comprising the steps of:
   counting the number of particles in each class of visually discernible characteristic prior to said editing step; and
   recounting the number of particles in each class of visually discernible characteristic based upon said editing step.

8. The method of claim 7, wherein said recounting step further comprises
   multiplying the count of the number of particles by a fraction whose denominator is the number of images of particles displayed and whose numerator is the number of images of particles which remain displayed after the editing step.

9. The method of claim 1 further comprising the step of
   processing each of said electronic images prior to said extracting step.

10. The method of claim 1 further comprising the step of
    processing each of the images of said particles after said extracting step.

11. The method of claim 1 wherein said extracting step further comprises:
    forming a resultant image comprising a plurality of images of said particles in an ordered array by classes of visually discernible characteristics; and
    said displaying step comprising:
    displaying said resultant image.

12. The method of claim 11 wherein
said resultant image comprises a plurality of images of particles of certain classes of visually discernible characteristics.

13. The method of claim 11 wherein said resultant image comprises a plurality of images of particles, having an a priori determined class of particles the images of which are removed from the forming step.

14. A method of analyzing particles from a moving fluid sample containing said particles comprising:
moving said sample in a direction of flow;
distributing said fluid sample over an extended area having a width and a thickness both measured perpendicular to the direction of flow, with substantially no particle overlapping other particles;
illuminating said fluid sample at a predetermined location in the direction of flow, with said illumination directed in a direction substantially perpendicular to the direction of flow;
forming a plurality of optical still images of said fluid sample, including said particles, at said location;
converting each of said optical still images to an electronic image thereby converting optical still images of said particles into electronic images of said particles;
extracting images of said particles from said electronic images;
displaying said electronic images of said particles in an ordered array by classes of visually discernible characteristics.

15. The method of claim 14, wherein one of said visually discernible characteristics is size of said particles.

16. The method of claim 14, wherein one of said visually discernible characteristics is color of said particle.

17. The method of claim 14, wherein one of said visually discernible characteristics is shape of said particle.

18. The method of claim 14, wherein one of said visually discernible characteristics is texture of said particle.

19. The method of claim 14 further comprising the step of
editing said display of said images of said particles.

20. The method of claim 19 further comprising the steps of:
counting the number of particles in each class of visually discernible characteristic prior to said editing step; and
recounting the number of particles in each class of visually discernible characteristic based upon said editing step.

21. The method of claim 20, wherein said recounting step further comprises
multiplying the count of the number of particles by a fraction whose denominator is the number of images of particles displayed and whose numerator is the number of images of particles which remain displayed after the editing step.

22. The method of claim 14 further comprising the step of
processing each of said electronic images prior to said extracting step.

23. The method of claim 14 further comprising the step of
processing each of the images of said particles after said extracting step.

24. The method of claim 14 wherein said extracting step further comprising:
forming a resultant image comprising a plurality of images of said particles in an ordered array by classes of visually discernible characteristics; and
said displaying step comprising:
displaying said resultant image.

25. The method of claim 24 wherein said resultant image comprises a plurality of images of particles of certain classes of visually discernible characteristics.

26. The method of claim 24 wherein said resultant image comprises a plurality of images of particles, having at least one a priori determined class of particles the images of which are removed from the forming step.

* * * * *